United States Patent [19]
Gross et al.

[11] Patent Number: 5,483,057
[45] Date of Patent: Jan. 9, 1996

[54] GLASS COLOR SENSOR UNIT

[75] Inventors: Michael Gross; Norbert Stelte, both of Überlingen; Dietmar Schmidt, Uhldingen-Mühlhofen; Hans Kordulla, Owingen, all of Germany

[73] Assignee: Bodenseewerk Geratetechnik GmbH, Uberlingen/Bodensee, Germany

[21] Appl. No.: 269,510

[22] Filed: Jul. 1, 1994

[30]    Foreign Application Priority Data

Jul. 9, 1993 [DE] Germany .......................... 43 22 865.8

[51] Int. Cl.⁶ ................. G01J 3/50; H01J 5/16; H01J 40/14
[52] U.S. Cl. .................. 250/226; 356/411; 209/580
[58] Field of Search .................. 250/226; 356/411; 209/582, 581, 580

[56]              References Cited

U.S. PATENT DOCUMENTS

| | | | |
|---|---|---|---|
| 3,499,527 | 3/1970 | Badgley | 209/581 |
| 3,980,180 | 9/1976 | Jamieson. | |
| 4,076,979 | 2/1978 | Walter et al. | 250/226 |
| 4,120,402 | 10/1978 | Swanson | 209/75 |
| 4,281,933 | 8/1981 | Houston et al. | 356/425 |
| 4,295,042 | 10/1981 | Watanabe et al. | 250/226 |
| 4,558,786 | 12/1985 | Lane | 209/558 |
| 4,678,338 | 7/1987 | Kitta et al. | 356/402 |
| 4,878,582 | 11/1989 | Codding | 209/580 |
| 4,919,534 | 4/1990 | Reed | 356/73 |
| 5,314,071 | 5/1994 | Christian et al. | 209/4 |
| 5,314,072 | 5/1994 | Frankel et al. | 209/44.1 |
| 5,318,172 | 6/1994 | Kenney et al. | 209/254 |
| 5,333,739 | 8/1994 | Stelte | 209/582 |

*Primary Examiner*—Edward P. Westin
*Assistant Examiner*—Stephen Caldgero
*Attorney, Agent, or Firm*—Lowe, Price, LeBlanc & Becker

[57]              ABSTRACT

Apparatus for measuring the color of glass, particularly pieces of broken glass relies upon simultaneously measuring the glass transmission in different spectral regions. The glass pieces travel along a conveying path between a light source and a light sensor containing a plural number of optical filters and groups of photoelectric detectors. The groups of photoelectric detectors are disposed at an end face of respective substantially cylindrical tubes. Tube axes enclose an angle and intersect in a conveying plane defined by the conveying path. The optical filters have different spectral transmission regions. Optical lens systems are retained intermediate the respective groups of photoelectric detectors and an opposite end face of the respective tubes. Each optical lens system images the conveying plane at the associated group of photoelectric detectors.

6 Claims, 6 Drawing Sheets

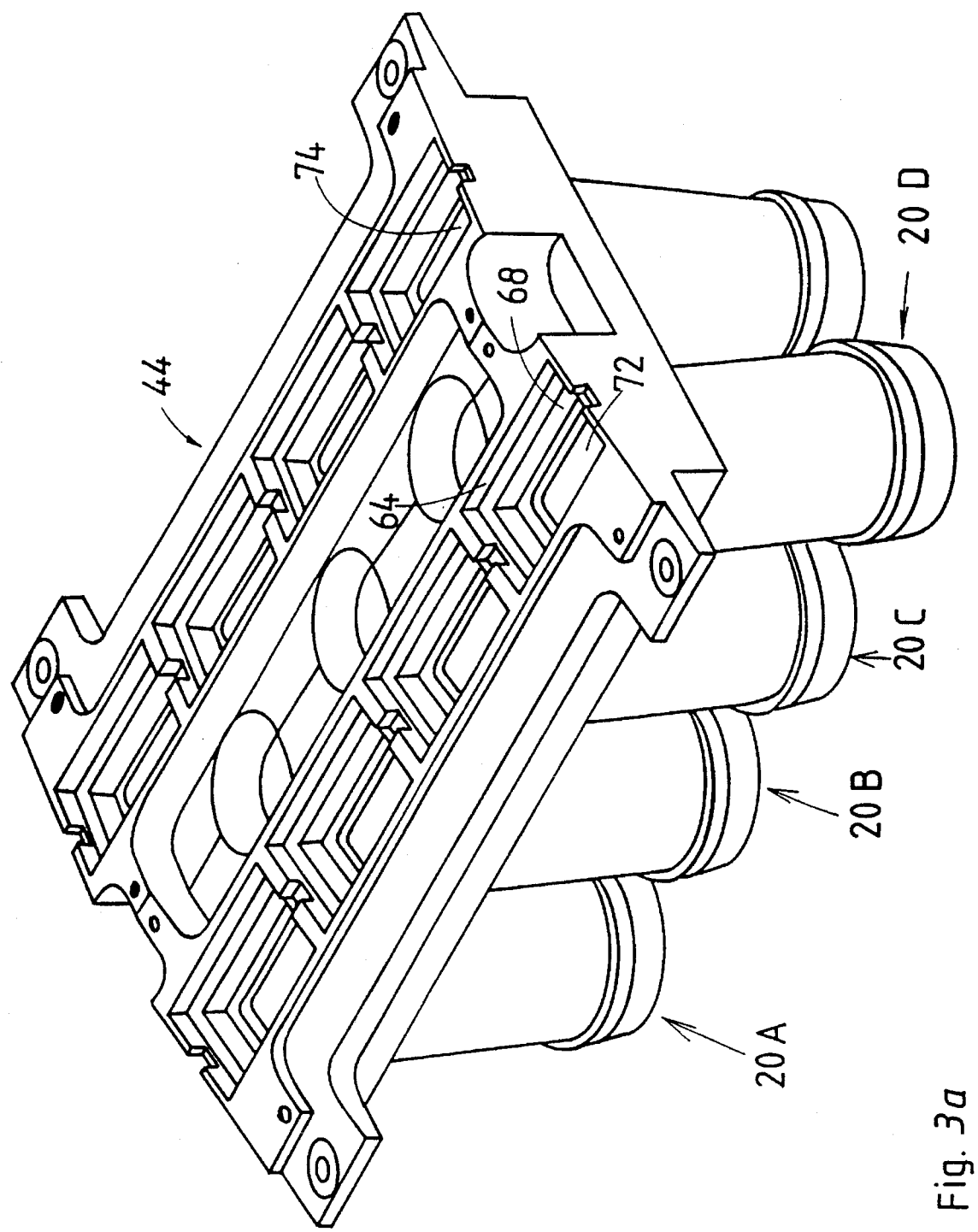

5,483,057

GLASS COLOR SENSOR UNIT

CROSS-REFERENCE TO RELATED APPLICATION

This application is related to the commonly assigned, copending U.S. patent application Ser. No. 08/035,480, filed Mar. 24, 1993, entitled "Method and Device of Sorting Bulk Material".

BACKGROUND OF THE INVENTION

The present invention relates to a new and improved construction of apparatus for measuring the color of glass, particularly broken glass.

In its more specific aspects, the present invention particulaly relates to a new and improved construction of apparatus for measuring the color of glass, particularly broken glass pieces and which apparatus includes means for simultaneousy measuring the transmission of the glass pieces in different spectral regions. The glass pieces are passed along a conveying path which extends between a light source and a light sensor or sensor head containing a plural number of optical filters and associated photoelectric detectors.

A sorting apparatus such as known, for example, from U.S. Pat. No. 3,980,180, granted Sep. 14, 1976, includes a belt conveyor receiving single glass particles in depressions which are aligned with apertures provided in the belt conveyor. The belt conveyor passes a sensing station containing light sources on one side of the belt conveyor and light detectors located on the opposite side of the belt conveyor so that light transmitted by the glass particles is detected. The light sources and the light detectors are selected so as to respectively emit and sense light of a narrow band width in a manner such that the intensity of the light transmitted by the glass particles is indicative of the color of the glass particles. The sensing station is followed in the conveying direction of the belt conveyor by a separating station which is provided with corresponding sensing means and compressed air nozzles producing an air jet for blowing away into a collecting container any glass particles having a predetermined color. A number of such sensing and separating stations may be arranged in series along the belt conveyor such that each of the combinations is responsive to a different color; also, a single sensing station may be provided to operate on a number of series-arranged separating stations.

The known installation is rather cumbersome and requires a comparatively large number of elements which tends to increase the danger of malfunction and/or failures.

SUMMARY OF THE INVENTION

Therefore, with the foregoing in mind, it is a primary object of the present invention to provide a new and improved construction of apparatus for measuring the color of glass, particularly broken glass pieces, and which apparatus is not afflicted with the drawbacks and limitations of the prior art constructions heretofore discussed.

Another and more specific object of the present invention is directed to the provision of a new and improved construction of apparatus for measuring the color of glass, particularly broken glass pieces, and which apparatus is of comparatively simple construction and thus less prone to malfunction and/or failure.

It is another important object of the present invention to provide a new and improved construction of apparatus for measuring the color of glass, particularly broken glass pieces, and which apparatus has a favorable price.

Now in order to implement these and still further objects of the invention, which will become more readily apparent as the description proceeds, the apparatus of the present development is manifested by the features that, among other things, (a) groups of photoelectric detectors are arranged at an end face of respective substantially cylindrical tubes,
(b) the tubes define axes which enclose a predetermined angle and which intersect in a conveying plane defined by the conveying path,
(c) optical lens systems are retained in the respective tubes, each optical lens system imaging the conveying plane defined by the conveying path at an associated group of photoelectric detectors, and
(d) optical filters precede the respective groups of photoelectric detectors and have different spectral transmission regions.

Thus completely separated paths of rays are provided for the different transmission ranges or spectral regions. However, the mirror-image relationship in the arrangement of the paths of rays will ensure that the detected light originates from the same location of the glass pieces.

BRIEF DESCRIPTION OF THE DRAWINGS

The invention will be better understood and objects other than set forth above, will become apparent when consideration is given to the following detailed description thereof. Such description makes reference to the attached drawings wherein the same or analogous components are designated by the same reference characters and wherein:

FIGS. 3a to 3c are perspective illustrations of a structural unit including four receiver units of the type as shown in FIG. 2 and arranged in juxtaposition relative to each other and transverse to a conveying direction.

DETAILED DESCRIPTION OF THE PREFERRED EMBODIMENTS

Figure 1:
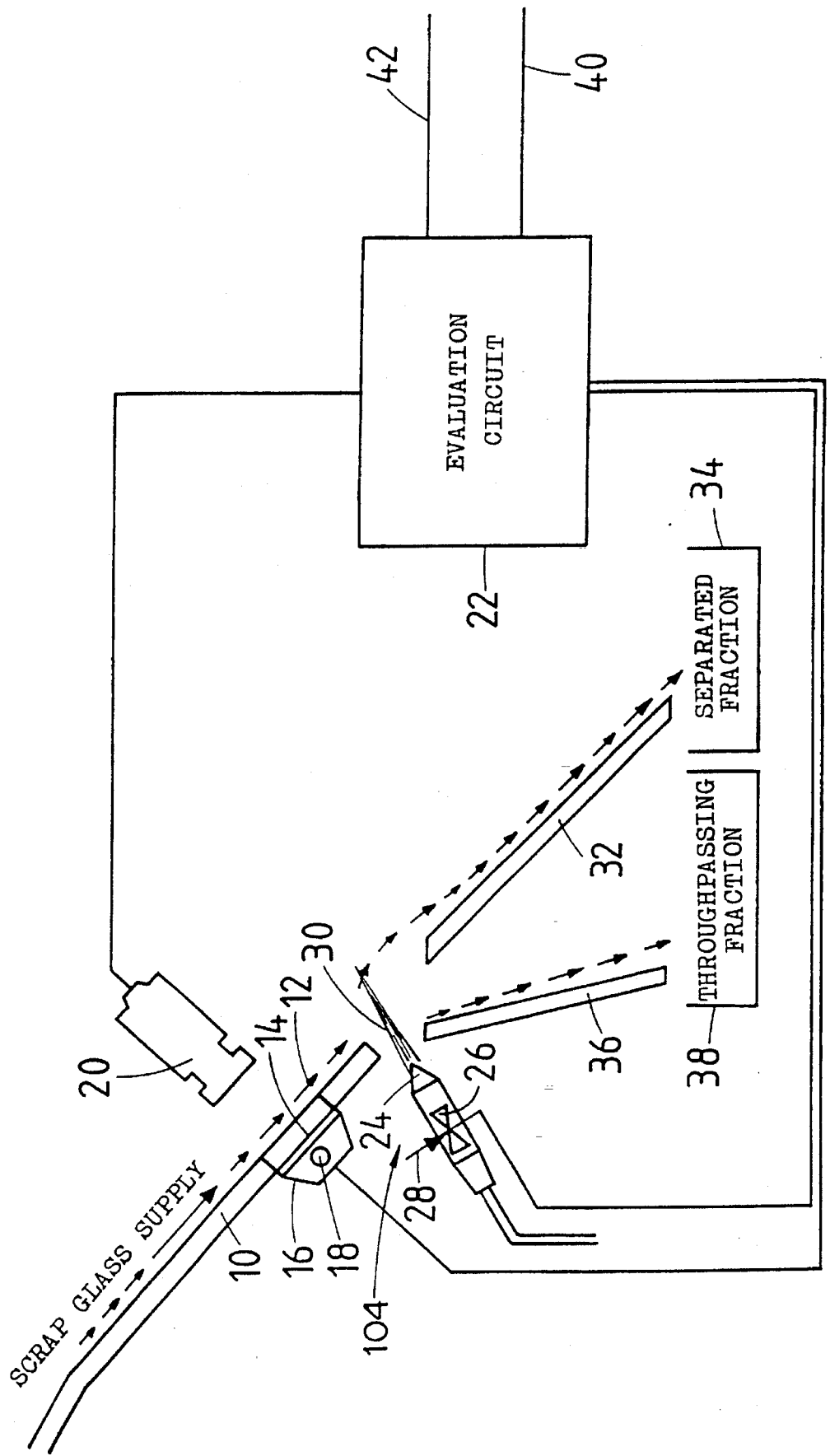
FIG. 1 schematically shows the basic structure of an exemplary embodiment of the inventive apparatus when used for classifying scrap glass according to color in two fractions.

Describing now the drawings, it is to be understood that only enough of the construction of the apparatus for measuring the color of glass has been shown as needed for those skilled in the art to readily understand the underlying principles and concepts of the present development while simplifying the showing of the drawings. Turning attention now to FIG. 1 of the drawings, there is schematically shown therein a conveying path designated by the reference character 10. In the illustrated exemplary embodiment, the conveying path 10 has the form of a slide or chute but may have any other suitable structure for conveying the glass, particularly broken glass pieces, in a manner such as to permit its investigation by the color sensing means described further hereinbelow. As stated, scrap glass or broken glass is conveyed along the slide or chute 10 in a conveying direction indicated by the arrows 12.

The conveying path, i.e. the slide or chute 10 has incorporated therein a plate 14 for diffusively transmitting light which originates from a reflector 16 placed below the plate 14. The reflector 16 is associated with an elongate light source 18 extending substantially transverse across the conveying path, i.e. the slide or chute 10. The light source 18 constitutes, for example, a fluorescent lamp which emits substantially white light.

The emitted light passes through the scrap or broken glass pieces which pass along the conveying path, i.e. the slide or chute 10 and which are substantially uniformly illuminated by means of the diffusively light transmitting plate 14. The throughpassed light is detected by means of a light sensor or sensing head 20 which is constructed in a manner such as to sense the light intensity in two different spectral regions. An evaluation circuit 22 is connected to the output side of the sensor or sensing head 20 and selectively associates respective pieces of scrap or broken glass with either a throughpassing fraction or a fraction to be separated in accordance with the transmitted light intensity detected in the two spectral regions. Details of the manner in which the transmitted light intensity is related to the color of the glass pieces are described in the initially cross-referenced U.S. patent application which is incorporated herein by reference.

The evaluation circuit 22 controls an effector system 104 composed of a plural number of effectors 24,26 each of which includes a compressed air nozzle 24 and a valve 26 governing the air nozzle 24. The valve 26 is supplied with compressed air through a connector 28. The compressed air is selectively either shut off or passed to the nozzle 24 through the valve 26, which is controlled by the evaluation circuit 22. A multiple number of the just described effectors 24,26 is arranged in a row to form the effector system 104 which extends across the width of the conveying path, i.e. the slide or chute 10.

The effector system 104 as described hereinbefore is located at the end of the conveying path, i.e. the slide or chute 10. If the evaluated piece of scrap or broken glass is classified as "to be separated", the valve 26 is opened. An air jet 30 issuing from the compressed air nozzle 24, blows the piece of scrap or broken glass away so that such piece passes via a further slide or chute 32 into a container 34 for collecting the fraction to be separated. Otherwise, the piece of scrap or broken glass passes through and drops onto a still further slide or chute 36 and thereby into a further container 38 for collecting the throughpassing fraction. The evaluation circuit 22 receives classification parameters via a line or conductor 40. Data from the evaluation circuit 22 are supplied to a central control unit of the installation through a line or conductor 42.

Figure 2:
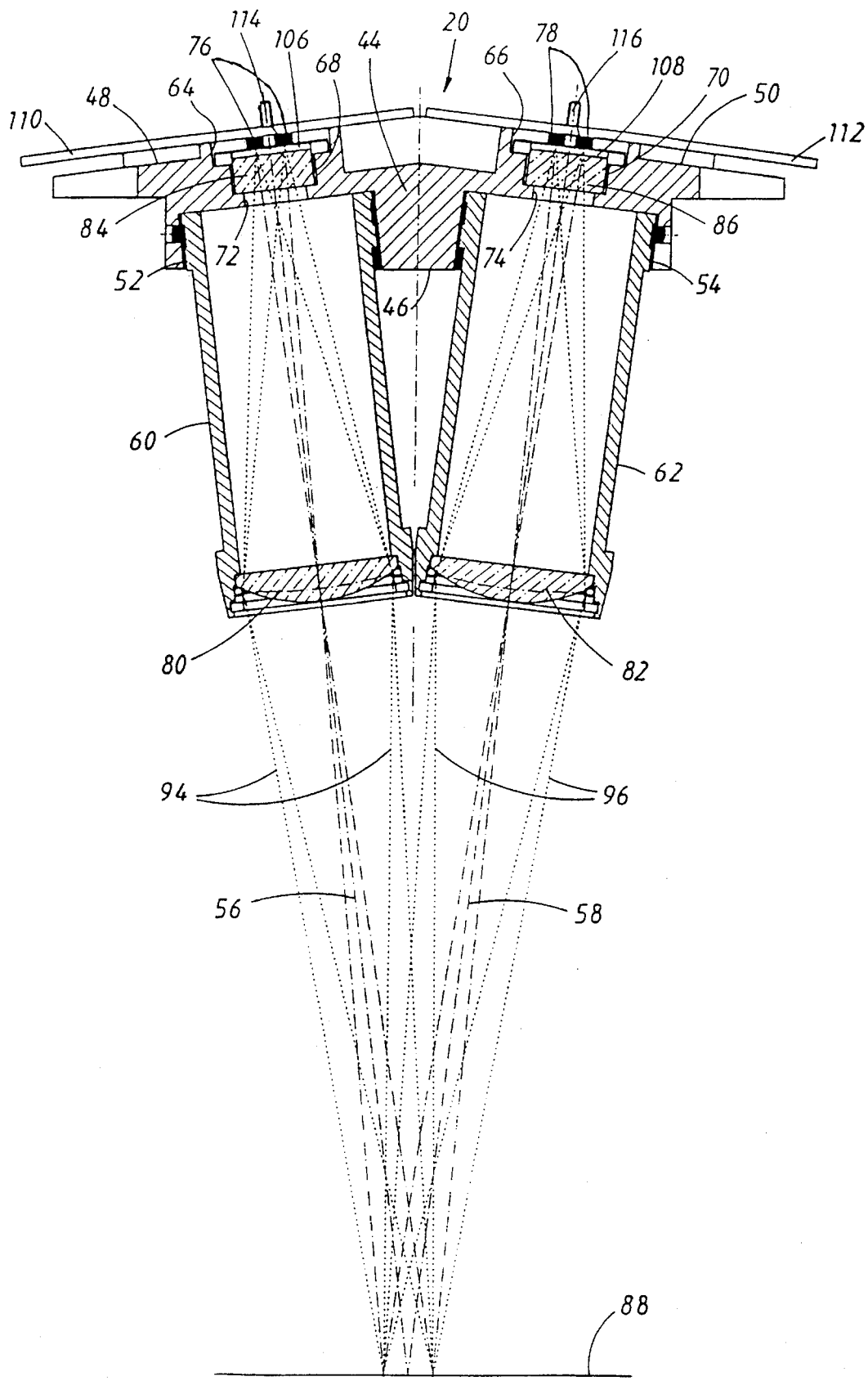
FIG. 2 is a section through a receiver unit of a light sensor in the apparatus as shown in FIG. 1.

FIG. 2 shows the light sensor or sensing head 20 which actually forms a unit for measuring in two spectral regions the light transmitted by the pieces of scrap or broken glass located below the light sensor or unit 20 on the conveying path, i.e. the slide or chute 10.

The light sensor or unit 20 includes a main body 44. The main body 44 defines a planar surface 46 on its bottom side facing a conveying plane 88 defined by the conveying path, i.e. the slide or chute 10. The main body 44 has a top side remote from the conveying path, i.e. the slide or chute 10. This top side is constructed in a roof-like manner by means of two members having top faces 48 and 50 which are inclined relative to each other and enclose an obtuse angle.

The respective bottom faces are provided with bores or cutouts 52 and 54 defining respective axes which enclose an angle and extend substantially perpendicular to the respective top faces 48 and 50. Tubes 60 and 62 are inserted into the respective bores or cutouts 52 and 54. The tubes 60 and 62 define respective lengthwise axes 56 and 58 which are substantially coincident with the axes of the associated bores or cutouts 52 and 54 and likewise form an angle with each other and intersect in the conveying plane 88 as defined by the conveying path, i.e. the slide or chute 10.

Extending from the top faces 48 and 50 of the main body 44 are respective shallow, substantially rectangular recesses 64 and 66 which are substantially centered relative to the axes 56 and 58 of the respective tubes 60 and 62. The recesses 64 and 66 are adjoined by respective, likewise substantially rectangular recesses 68 and 70 of smaller cross-section. The recesses 68 and 70 likewise are substantially centered relative to the axes 56 and 58 of the respective tubes 60 and 62. The recesses 68 and 70 are respectively connected through substantially rectangular apertures 72 and 74 with the bores or cutouts 52 and 54 and thus with the interior of the respective tubes 60 and 62. The apertures 72 and 74 likewise are substantially centered to the axes 56 and 58 of the respective tubes 60 and 62.

Photoelectric detectors 76 and 78 are respectively placed in the recesses 68 and 70. The arrangement is such that the photoelectric detectors are placed on top of the respective tubes 60 and 62 above the tp end faces remote from the conveying path, i.e. the slide or chute 10. Optical filters 84 and 86 are disposed in the respective substantially rectangular recesses 68 and 70 of smaller cross-section. The optical filters 84 and 86 are different from each other with respect to their optical or spectral transmission region as required for classification of the pieces of scrap or broken glass according to color, see also the initially cross-referenced U.S. patent application which is incorporated herein by reference.

Figure 3B:
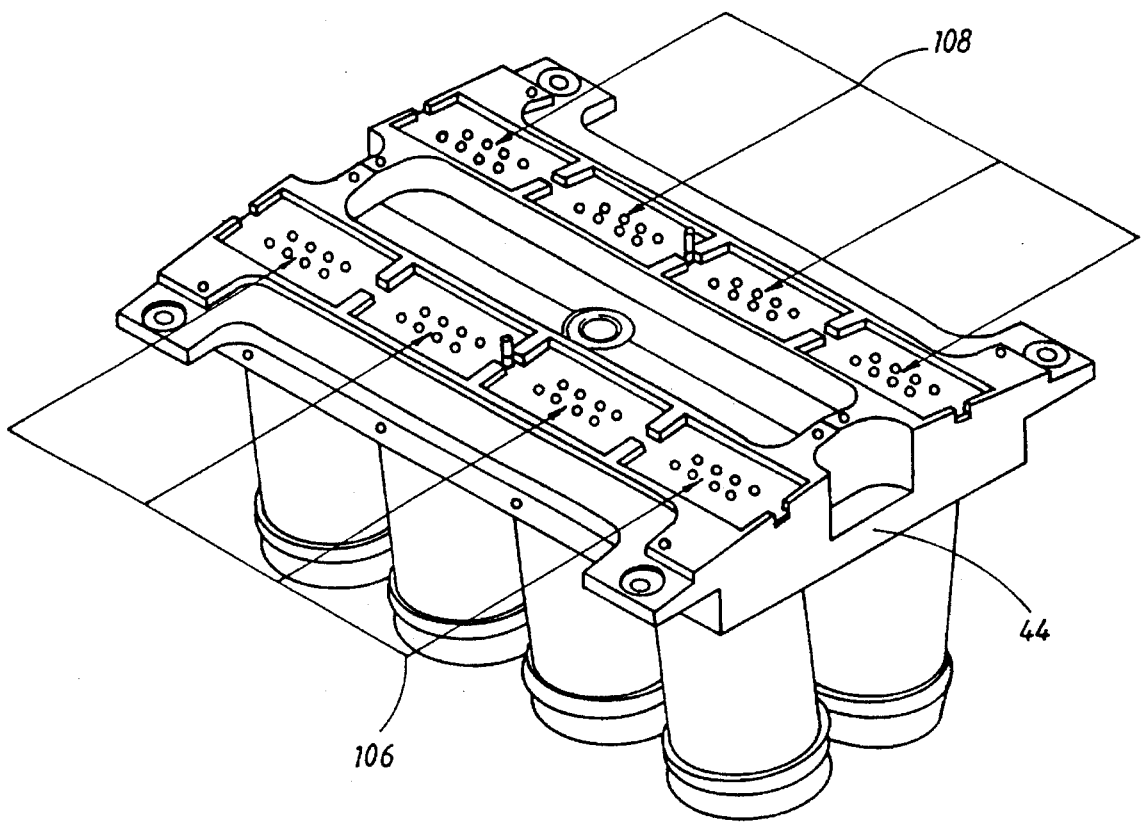

Apertured plates 106,108 are respectively located above the respective optical filters 84 and 86 as will be readily recognized in FIG. 3b the drawings. Each one of the apertured plates 106,108 contains two rows 100,102 of round holes which are disposed at an offset from each other. As will be further recognized in FIG. 3b, four apertured plates 106 and 108 are combined to form a structural unit whereby assemblage of the inventive apparatus will be considerably facilitated.

Figure 3C:
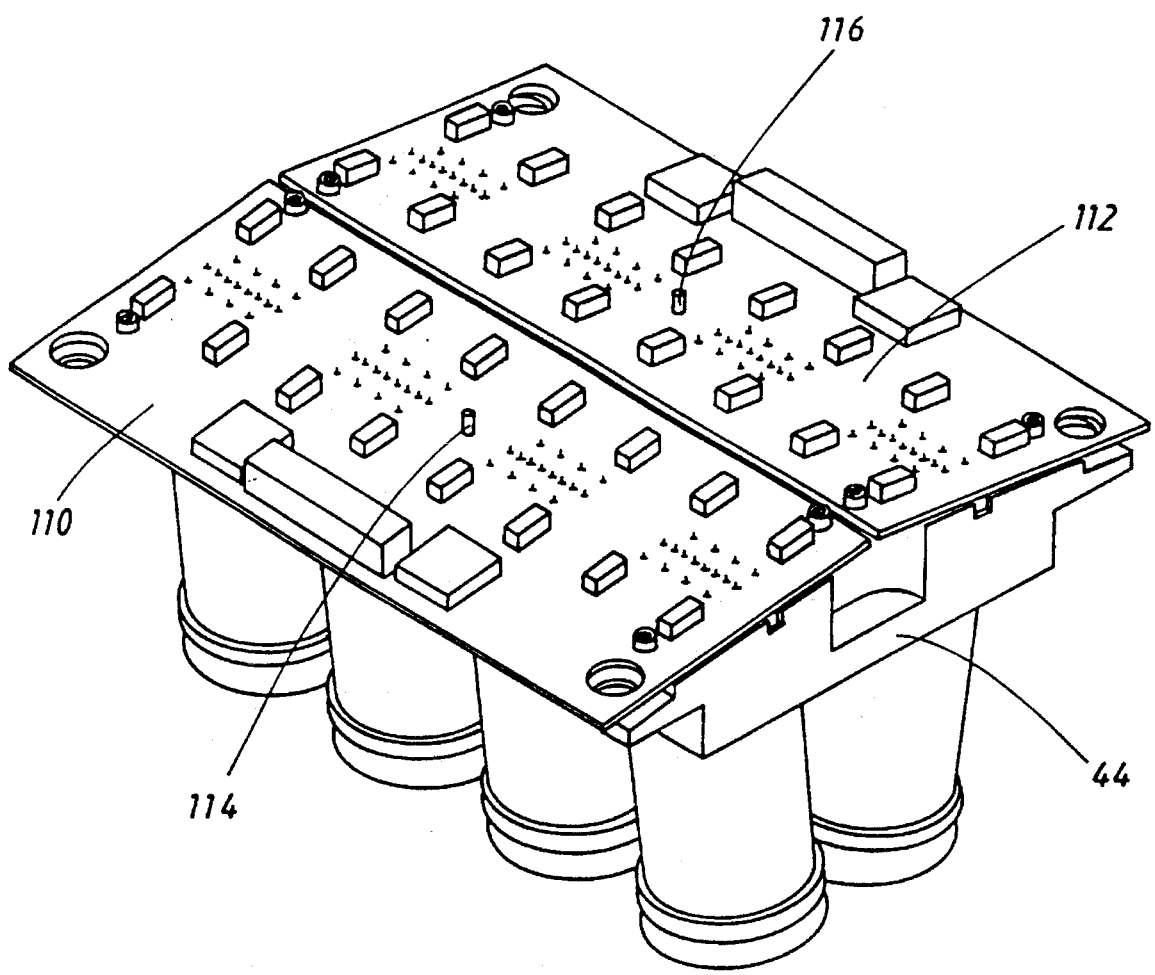

It will be recognized in FIG. 3c of the drawings that circuit boards 110 and 112 are disposed above the respective apertured plates 106,108 on the respective roof-like top faces 48 and 50 of the main body 44. On their bottom side, the circuit boards 110 and 112 support respective groups of photoelectric detectors 76 and 78, for example, phototransistors. These elements are arranged such as to be aligned with the holes in the apertured plates 106 and 108. The components placed on the top side of the circuit boards 110 and 112 are not specifically described but serve in conventional manner for operating the photoelectric detectors 76 and 78 located on the bottom side of the circuit boards 110 and 112.

Centering pins 114 and 116 serve for substantially centering the respective circuit boards 110,112 at the main body 44 or the respective roof-like top faces 48 and 50.

Imaging optical lens systems 80 and 82 are respectively placed in the lower ends of the tubes 60 and 62 such as to face the conveying plane 88 defined by the conveying path, i.e. the slide or chute 10. As will be seen in FIG. 2 of the drawings, the axes 56 and 58 of the respective tubes 60 and 62 also define optical axes of the respective optical lens systems 80 and 82. The optical axes likewise intersect essentially in the conveying plane 88 defined by the conveying path, i.e. the slide or chute 10, or slightly above thereof at the surface of the pieces of scrap or broken glass passed along the conveying path, i.e. the slide or chute 10. This conveying plane 88 is imaged by the optical lens systems 80 and 82 at the associated photoelectric detectors 76 and 78. The border rays of respective imaging light beams 94 and 96 are illustrated in FIG. 2.

As will be apparent from FIG. 3a of the drawings, the light sensor or unit 20 encompasses a total of four receiver units 20A,20B,20C,20D provided at the main body 44 which constitutes a common support body for such receiver units. As shown in FIG. 2, each one of the receiver units 20A,20B,20C, 20D comprises two substantially cylindrical tubes 60 and 62 inclusive of the associated imaging optical lens system 80,82, the optical filters 84 and 86 and the photoelectric detectors 76 and 78. The two substantially cylindrical tubes 60 and 62 of the receiver units 20A,20B, 20C, 20D are seen to be arranged above the conveying path, i.e. the slide or chute 10 in juxtaposition in the conveying direction 12. It will also be apparent from these drawings that the light sensor or unit 20 is composed of two rows of such tubes 60 and 62 or receiver units 20A,20B,20C,20D in a manner such that the two rows extend essentially transverse to the conveying direction 12 or across the width of the conveying path, i.e. the slide or chute 10. Since the photoelectric detectors 76 and 78 are aligned with the apertured holes in the apertured plates 106,108 which are placed above the top end face of the substantially cylindrical tubes 60 and 62, groups of photoelectric detectors 76 and 78 are respectively associated with the two rows of substantially cylindrical tubes 60 and 62. Each group of photoelectric detectors 76 and 78 likewise encompasses two rows arranged at an offset in a staggered relationship corresponding to the arrangement of holes in the apertured plates 106,108.

Figure 4:
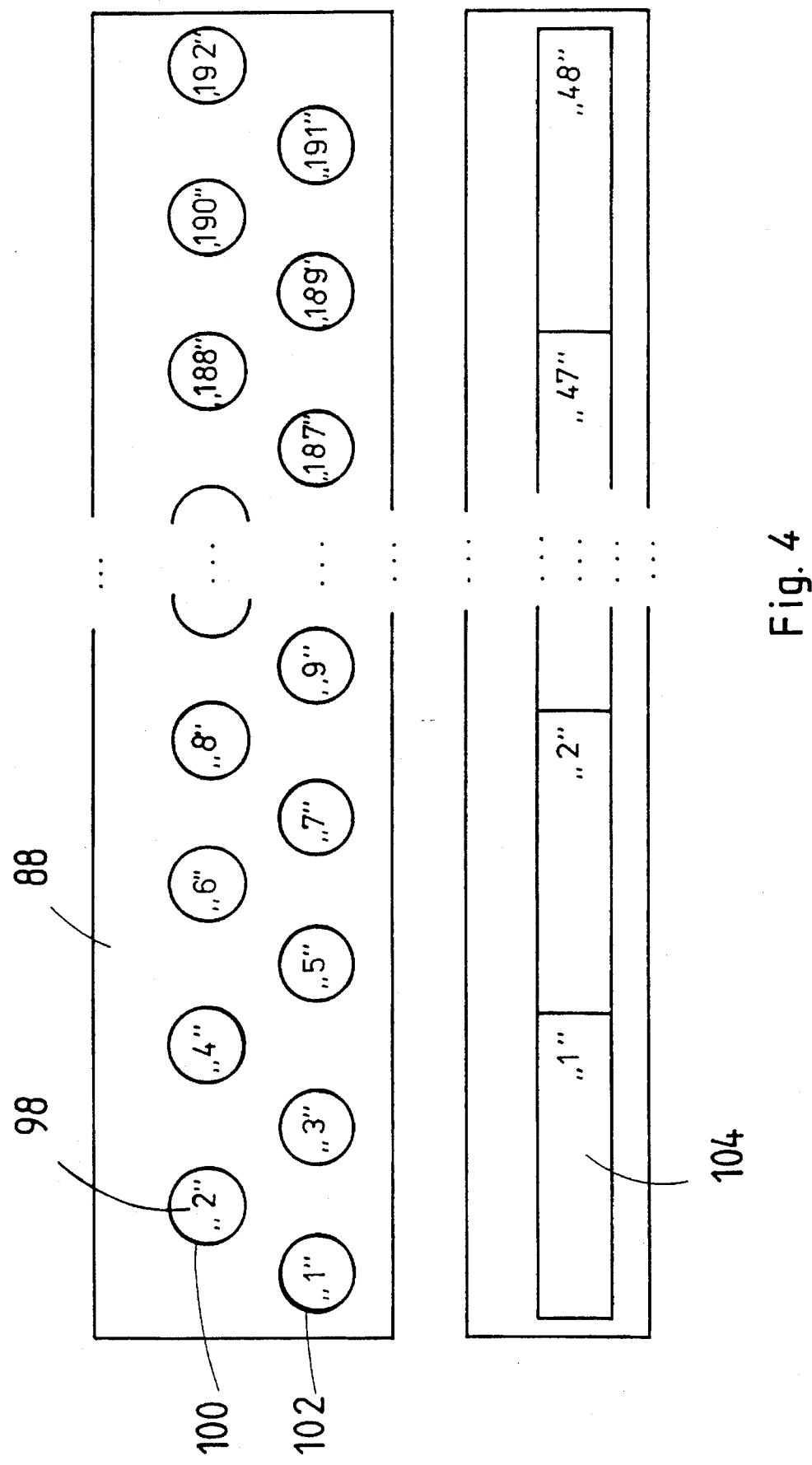
FIG. 4 is a schematic top plan view of two mutually offset rows of substantially circular areas of the conveying path, which areas are imaged at the photoelectric detectors, and an effector system for carrying out a separating operation.

FIG. 4 of the drawings shows 192 substantially circular areas 98 located in the conveying plane 88 defined by the conveying path, i.e. the slide or chute 10 and the substantially circular areas 98 are under observation by the groups of photoelectric detectors 76 and 78. In order to completely cover the entire width of the conveying path, i.e. the slide or chute 10, two substantially parallel rows 100 and 102 of the substantially circular areas 98 are provided and offset from each other. The rows 100 and 102 are mutually offset from each other such that the areas 98 assume a staggered relationship with respect to each other in a manner generally comparable to the staggered arrangement of holes in the apertured plates 106,108 and the groups of photoelectric detectors 76,78.

FIG. 4 of the drawings also shows the position and alignment of the effector system 104 relative to the conveying plane 88 defined by the conveying path, i.e. the slide or chute 10. Four of the substantially circular areas 98 under observation activate a respective one of 48 effectors 1 to 48 which conjointly form the effector system 104. Thus the effector 1 is associated with the substantially circular areas 98 marked "1", "2", "3" and "4" and thus is controlled by the photoelectric detectors 76,78 located in the receiver unit 20A or 20D, as the case may be.

The evaluation circuit 22 stores a control command controlling the effector system 104 and permits activating selected ones or all of the effectors 1 to 48 at a delay which is determined by the conveying speed of the pieces of scrap or broken glass on the conveying path, i.e. the slide or chute 10, and the spacing between the receiver units 20A,20B, 20C,20D and the effectors 1 to 48.

While there are shown and described present preferred embodiments of the invention, it is to be distinctly understood that the invention is not limited thereto, but may be otherwise variously embodied and practiced within the scope of the following claims. Accordingly,

What we claim is:

1. A sensor unit for measuring the color of glass moving past in a conveying plane on a conveying path, comprising:

a set of first substantially cylindrical tubes defining respective lengthwise axes, a set of second substantially cylindrical tubes defining respective lengthwise axes, each first tube forming a pair with an associated second tube, the axes of said first and second tubes of each pair intersecting and forming an angle, said intersecting axes defining a longitudinal plane, a plurality of said pairs being arranged side by side transversely to said longitudinal planes, each of said tubes holding an optical lens system, one filter and being aligned with a group of photoelectric detectors, said photoelectric detectors of said group being arranged in two staggered rows transverse to said longitudinal plane, the transmission characteristics of said filters in said first tubes being different from the transmission characteristics of the filters in said second tubes, the optical systems and photoelectric detectors of said first and second tubes of each pair being arranged to image each detector of said first tube substantially at the same location as an associated detector of said second tube, whereby, in turn, said same location is imaged on both detectors, said axes of all pairs of tubes intersecting on a straight line transverse to said longitudinal planes and lying in a plane, said images of said detectors being formed in said plane along said straight line.

2. A sensor unit as claimed in claim 1, and further comprising:

a main body having first and second sides, said main body, on its first side, being provided with bores for receiving said pairs of substantially cylindrical tubes, said bores having bore axes coinciding with said lengthwise axes of the respective ones of said tubes, said main body, on said second side, defining two roof-like faces which extend substantially perpendicular to said lengthwise axes of said first and second tubes, respectively, said two roof-like faces containing respective apertures substantially centered relative to said substantially cylindrical tubes received in said bores, said apertures accommodating said filters and said photoelectric detectors.

3. A sensor unit as claimed in claim 2, wherein:

said apertures in said roof-like faces are rectangular, stepped apertures, each having a relatively large outer portion adjacent the respective one of said faces, a median portion of smaller dimensions and a still smaller inner portion, said median portion accommodating said filter, said outer portion accommodating a light stop having two staggered rows of apertures therethrough, and said photoelectric detectors being mounted, in alignment with said apertures, on circuit boards placed on said roof-like faces, said photoelectric detectors extending into the respective ones of said outer portions of said apertures.

4. A sensor unit as defined in claim 1, wherein:

said sensor unit contains a multiple number of receiver units;

said conveying path defining a conveying direction; and said first and second substantially cylindrical tubes of said multiple number of receiver units being located in juxtaposed relationship to each other in said conveying direction.

5. The apparatus as defined in claim 4, wherein:

each one of said multiple number of receiver units includes a main body;

said main body defining a bottom side facing said conveying path;

said main body, on said bottom side facing said conveying path, being provided with bores for receiving respective ones of said at least one pair of first and second substantially cylindrical tubes;

said first and second substantially cylindrical tubes defining respective lengthwise axes;

said bores extending at a predetermined inclination relative to each other and defining respective axes;

said main body defining a top side remote from said conveying path;

said main body, on said top side remote from said conveying path, defining two roof-like top faces which extend substantially perpendicular to respective ones of said axes defined by said bores and said first and second substantially cylindrical tubes received in said bores;

said two roof-like top faces containing respective apertures substantially centered relative to said first and second substantially cylindrical tubes received in said bores; and said apertures receiving respective ones of said plural number of photoelectric detectors.

6. The apparatus as defined in claim 5, wherein:

said multiple number of receiver units contain a plurality of pairs of said first and second substantially cylindrical tubes;

said plurality of said pairs of said first and second substantially cylindrical tubes defining two rows extending substantially transverse to said conveying direction;

each one of said two rows of said first and second substantially cylindrical tubes containing one of said groups of photoelectric detectors; and each one of said groups of photoelectric detectors forming two rows of photoelectric detectors which rows are arranged in a staggered relationship relative to each other and substantially transverse to said conveying direction.

\* \* \* \* \*